(12) United States Patent
Beck

(10) Patent No.: US 6,358,680 B1
(45) Date of Patent: Mar. 19, 2002

(54) DETECTION OF WHEAT AND BARLEY FUNGAL PATHOGENS USING THE POLYMERASE CHAIN REACTION

(75) Inventor: James Joseph Beck, Cary, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/026,601

(22) Filed: Feb. 20, 1998

(51) Int. Cl.$^7$ .......................... C12Q 1/68; C12P 19/34; C07H 21/02; C07H 21/04
(52) U.S. Cl. ...................... 435/6; 435/91.2; 536/24.32; 536/24.33; 536/23.1
(58) Field of Search ................. 435/6, 91.2; 536/24.32, 536/24.33, 23.1

(56) References Cited

U.S. PATENT DOCUMENTS

| | | | |
|---|---|---|---|
| 5,635,353 A | 6/1997 | Lott et al. ...................... | 435/6 |
| 5,688,644 A | 11/1997 | Lott et al. ...................... | 435/6 |
| 5,827,695 A | 10/1998 | Beck ........................ | 435/91.2 |

FOREIGN PATENT DOCUMENTS

| | | |
|---|---|---|
| EP | 0 859 061 A2 | 8/1998 |
| WO | WO 95/29260 | 2/1995 |

OTHER PUBLICATIONS

Myers, R. M.. GenBank Accession No. G17470. Mar. 05, 1996.*
Peltonen et al. Ann. Appl. Biology. 128:465–477, 1996.*
White et al. PCR Protocols: A Guide to Methods and Applications. Academic Press Inc., New York, pp. 315–322, 1990.*
Stevens et al., Seed Health Testing, CAB International, XP–002104980, 139–145 (1997).
GenBank Accession No. XP–002104981, 1–2, Jan. 17, 1997.
Alderson et al., National Institute of Agricultural Botany, Molecular Biology and Diagnostics Section, Abstract No. XP–002104977 (1995).
Genbank Accession No. XP–002104982, 1–2, Feb. 5, 1997.
Genbank Accession No. XP–002104983, 1–2, Feb. 5, 1997.
Genbank Accession No. XP–002104984, 1 page, Mar. 27, 1992.
Genbank Accession No. XP–002104985, 1 page, Aug. 7, 1997.
International Search Report, PCT/EP99/01058, 1–5, Feb. 18, 1999.
De Wolf and Francl, "Neural Networks that Distinguish Infection Periods of Wheat Tan Spot in an Outdoor Environment", *Phytopathology* 87: 83–87 (1997).
Kwon et al., "A Quantitative Bioassay for Necrosis Toxin from *Pyrenophora tritici–repentis* Based on Electrolyte Leakage", *Phytopathology* 86: 1360–1363 (1996).
Stevens et al., "Development of a Multiplex PCR Seed Health Test to Detect and Differentiate Three Pathogens of Barley", 1996 BCPC Symposium Proceedings No. 65: Diagnostics in Crop Production.

* cited by examiner

*Primary Examiner*—Carla J. Myers
(74) *Attorney, Agent, or Firm*—Mary Kakefuda; J. Timothy Meigs

(57) ABSTRACT

Internal Transcribed Spacer (ITS) DNA sequences from the ribosomal RNA gene region are described for species and strains of wheat fungal pathogens, including *Pyrenophora tritici-repentis* and *Pyrenophora teres*. Specific primers from within these sequences are identified as being useful for the identification of the fungal isolates using PCR-based techniques.

20 Claims, No Drawings

DETECTION OF WHEAT AND BARLEY FUNGAL PATHOGENS USING THE POLYMERASE CHAIN REACTION

FIELD OF THE INVENTION

The present invention relates to the use of primers in polymerase chain reaction assays for the detection of fungal pathogens in wheat and barley. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; *Proc. 1981 Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

Wheat is currently the most important agricultural commodity in international markets and occupies about 20% of the world's farmed land (1977; Compendium of Wheat Diseases, Amer. Phytopath. Soc. page 1). Eightly percent of the world's supply of wheat is grown in North America, Europe, China, and the Soviet Union. Approximately 20% of the worldwide production of wheat is lost to disease annually.

*Pyrenophora tritici-repentis* (Died.) Drechs. (syn. *P. trichostoma* (Fr.) Fckl.), anamorph Drechslera tritici-repentis (Died.) Shoem. (syn. *Helminthosporium tritici-repentis* Died.), causes tan spot also known as yellow spot of wheat worldwide (1977; Compendium of Wheat Diseases, Amer. Phytopath. Soc. page 42). It has resulted in wheat yield losses from 3 to 50 % in Australia, South America, and North America and has been recently considered the most important foliar wheat disease in North Dakota (Zhang et al., 1997; Phytopathology. Vol.87:154–160). It can also contribute to leaf-spotting complexes with other foliar pathogens. Current disease control measures include fungicide application and cultural practices including destroying wheat stubble, using pathogen-free seed and wide row plant spacing to reduce foliage density and relative humidity in the wheat canopy.

*Pyrenophora teres* Drechs., anamorph *Drechslera teres* (Sacc.) Shoem. (syn. *Helminthosporium teres* Sacc.) causes net blotch primarily in barley; however, sporadic infections also occur in wheat (Jones and Clifford; Cereal Diseases, John Wiley, 1983). Typical yield losses due to net blotch are between 10 to 40%. Yield losses can approach 100% in fields containing susceptible cultivars (1982; Compendium of Barley Diseases, Amer. Phytopath. Soc. page 22). In addition to affecting overall grain yield and weight, the disease also reduces the carbohydrate content. This reduces malt extract yield and therefore lowers the brewing quality of the grain.

In view of the above, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

In view of the above, a primary object of the invention is to provide a method for the identification of specific races of pathogen fungi early in the infection process. The invention therefore provides Internal Transcribed Spacer (ITS) DNA sequences that show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

In a preferred embodiment, the invention provides novel ITS1 and ITS2 DNA sequences for the fungal pathogen *Pyrenophora tritici-repentis*. In another preferred embodiment, the invention provides ITS-derived diagnostic primers for the detection of *Pyrenophora tritici-repentis*. In an additional preferred embodiment, the invention provides novel ITS-derived diagnostic primers that are useful for the detection of not only *Pyrenophora tritici-repentis*, but also, surprisingly, *Pyrenophora teres* and *Drechslera sorokiniana*. The present invention therefore addresses a long-felt but unfulfilled need to identify different pathotypes of plant pathogenic fungi, especially those that cause tan spot in wheat.

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of the fungal pathogen *Pyrenophora tritici-repentis*.

BRIEF DESCRIPTION OF THE SEQUENCES IN THE SEQUENCE LISTING

SEQ ID NO:1 Oligonucleotide Primer ITS1.
SEQ ID NO:2 Oligonucleotide Primer ITS2.
SEQ ID NO:3 Oligonucleotide Primer ITS3.
SEQ ID NO:4 Oligonucleotide Primer ITS4.
SEQ ID NO:5 M13 Universal-20 Primer.
SEQ ID NO:6 Reverse Primer used in Example 2.
SEQ ID NO:7 Oligonucleotide Primer JB629.
SEQ ID NO:8 Oligonucleotide Primer JB630.
SEQ ID NO:9 Oligonucleotide Primer JB631.
SEQ ID NO:10 Oligonucleotide Primer JB632.
SEQ ID NO:11 Oligonucleotide Primer JB633.
SEQ ID NO:12 Oligonucleotide Primer JB634.
SEQ ID NO:13 Oligonucleotide Primer JB635.
SEQ ID NO:14 Oligonucleotide Primer JB636.
SEQ ID NO:15 Oligonucleotide Primer JB637.
SEQ ID NO:16 Oligonucleotide Primer JB638.
SEQ ID NO:17 Oligonucleotide Primer JB651.
SEQ ID NO:18 Oligonucleotide Primer JB652.
SEQ ID NO:19 Oligonucleotide Primer JB653.
SEQ ID NO:20 Oligonucleotide Primer JB654.
SEQ ID NO:21 Oligonucleotide Primer JB655.
SEQ ID NO:22 Oligonucleotide Primer JB656.
SEQ ID NO:23 Oligonucleotide Primer JB657.
SEQ ID NO:24 Oligonucleotide Primer JB658.
SEQ ID NO:25 Oligonucleotide Primer JB659.
SEQ ID NO:26 Oligonucleotide Primer JB660.
SEQ ID NO:27 Oligonucleotide Primer JB675.
SEQ ID NO:28 Oligonucleotide Primer JB676.
SEQ ID NO:29 Consensus DNA sequence of the ITS region from *Pyrenophora tritici-repentis* isolates 6715, 119-2-3, DL22, PTR4A, 44184, 205, 403, 109, 407, 1316, and 223, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:30 Consensus DNA sequence of the ITS region from *Pyrenophora tritici-repentis* isolate 6715 clones 2 and 4, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:31 DNA sequence of the ITS region from *Pyrenophora tritici-repentis* isolate 119-2-3 clone 2-2, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:32 DNA sequence of the ITS region from *Pyrenophora tritici-repentis* isolate DL22 clone 1-1, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:33 DNA sequence of the ITS region from *Pyrenophora tritici-repentis* isolate PTR4A clone 2-3, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:34 DNA sequence of the ITS region from *Pyrenophora tritici-repentis* isolate 44184 clone 3-1, comprising in the 5'to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:35 DNA sequence of the ITS region from *Pyrenophora tritici-repentis* isolate 205 clone 4-2, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:36 DNA sequence of the ITS region from *Pyrenophora tritici-repentis* isolate 403 clone 5-2, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:37 DNA sequence of the ITS region from *Pyrenophora tritici-repentis* isolate 109 clone 6-2, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:38 DNA sequence of the ITS region from *Pyrenophora tritici-repentis* isolate 407 clone 7-3-2, comprising in the .5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:39 DNA sequence of the ITS region from *Pyrenophora tritici-repentis* isolate 1316 clone 8-1, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:40 DNA sequence of the ITS region from *Pyrenophora tritici-repentis* isolate 223 clone 9-2, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:41 DNA sequence of the ITS region from *Pyrenophora teres* isolate 36570 clone 10-1, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. These ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol* 57: 553–556), and random amplified polymorphic DNA (i.e. RAPD) markers were able to distinguish numerous races of *Gremmeniella abietina*, the causal agent of scleroderris canker in conifers. U.S. Pat. No. 5,585,238 (herein incorporated by reference in its entirety) describes primers derived from the ITS sequences of the ribosomal RNA gene region of strains of *Septoria, Pseudocercosporella,* and Mycosphaerella and their use in the identification of these fungal isolates using PCR-based techniques. In addition, U.S. patent application Ser. No. 08/722,187 (herein incorporated by reference in its entirety) describes primers derived from the ITS sequences of the ribosomal RNA gene region of strains of Fusarium and their use in the identification of these fungal isolates using PCR-based techniques. Furthermore, U.S. patent application Ser. No. 08/742,023 (herein incorporated by reference in its entirety) describes primers derived from the ITS sequences of the ribosomal RNA gene region of strains of Cercospora, Helminthosporium, Kabatiella, and Puccinia and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS 1 and ITS2, of around 300 bp (White et al., 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. After determining the ITS sequences of a pathogen, these sequences can be aligned with other ITS sequences. Primers can then be derived from the ITS sequences. That is, primers can be designed based on regions within the ITS sequences having the greatest differences in sequence among the fungal pathotypes. The sequences and primers based thereon can be used to identify specific pathogens.

Particular DNA sequences of interest include ITS DNA sequences from *Pyrenophora tritici-repentis* and *Pyrenophora teres*. Such ITS DNA sequences are disclosed in SEQ ID NOs: 29–41. Sequences of representative oligonucleotide primers derived from these ITS sequences are disclosed in SEQ ID NOs: 7–28. The sequences find use in the PCR-based identification of the pathogens of interest. Therefore, based on Applicants' disclosure of the present invention, the fungal pathogen responsible for tan spot in wheat can, for the first time, be detected by a PCR-based diagnostic assay.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol* 57:553–556. See also, Nazar et al. (1991; *Physiol and Molec. Plant Pathol.* 39: 1–11), which used PCR amplification to exploit differences in the ITS regions of *Verticillium albo-atrum* and *Verticillium dahliae* and therefore distinguish between the two species; and Johanson and Jeger (1993; Mycol. Res. 97: 670–674), who used similar techniques to distinguish the banana pathogens *Mycosphaerella fijiensis* and *Mycospharella musicola*.

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: PCR Protocols: A Guide to Methods and Applications, Innes et al. (Eds.); pages 282–287.

Alternatively, the ITS sequences of interest can be determined by PCR amplification. In an exemplified embodiment, primers to amplify the entire ITS region were designed according to White et al. (1990; In: PCR Protocols; Eds.: Innes et al. pages 315–322), and the amplified ITS sequence was subcloned into the pCRII cloning vector. The subcloned sequence included the left hand ITS (ITS 1), the right hand ITS (ITS2), as well as the centrally located 5.8S rRNA gene. This was undertaken for several isolates of *Pyrenophora tritici-repentis* and from a single isolate of *Pyrenophora teres*.

The determined ITS sequences were compared within each pathogen group to locate divergences that might be useful to test in PCR to distinguish the different species and/or strains. The ITS DNA sequences that were determined are shown in SEQ ID NOs: 29–41. From the identification of divergences, numerous primers were synthesized and tested in PCR-amplification. Templates used for PCR-amplification testing were firstly purified pathogen DNA, and subsequently DNA isolated from infected host plant tissue. Thus, it was possible to identify pairs of primers that were diagnostic, i.e. that identified one particular pathogen species or strain but not another species or strain of the same pathogen. Primers were also designed to regions highly conserved among the species to develop genus-specific primers as well as primers that identify any of several fungal pathogens that cause a certain disease. For example, primers were developed to detect both *P. teres* and *P. tritici-repentis*.

Preferred primer combinations are able to distinguish between the different species or strains in infected host tissue, i.e. host tissue that has previously been infected with a specific pathogen species or strain. This invention provides numerous primer combinations that fulfill this criterion for *P. teres* and *P. tritici-repentis*. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70° C. to achieve good sensitivity and should be void of significant secondary structure and 3' overlaps between primer combinations. Primers generally have sequence identity with at least about 5–10 contiguous nucleotide bases of ITS1 or ITS2. In preferred embodiments, primers are anywhere from about 5–30 nucleotide bases long and are preferably at least 10 nucleotide bases long.

As an alternative to the above-described PCR diagnostic techniques, a specific fungal DNA's ITS region can be used to design polynucleotide label probes, each comprising a label portion and a nucleic acid region having a sequence that is complementary to at least about 5–10 contiguous nucleotides of ITS 1 or ITS2. In preferred embodiments, the complementary nucleic acid regions of such probes are anywhere from about 5–30 nucleotide bases long and are preferably at least 10 nucleotide bases long. The label portion of the probes may comprise either a label that provides a signal or a binding site for such a label. Polynucleotide label probes such as these may be used in fungal detection methods that involve the following steps: (a) designing at least one polynucleotide label probe comprising a nucleic acid region having a sequence that is complementary to at least about 5–10 contiguous nucleotide bases of ITS1 or ITS2 of a fungal pathogen, such as *Pyrenophora tritici-repentis*, and a label portion comprising either a label that provides a signal when said probe hybridizes with another nucleic acid molecule or a binding site for said label; (b) isolating DNA from plant tissue infected with the fungal pathogen; (c) hybridizing the DNA of step (b) with the probe or probes of step (a); and (d) detecting the fungal pathogen by detecting the label, wherein detection of the label indicates that the hybridization of step (c) has occurred and the fungal pathogen is present. Labels may be designed and detected according to any means known in the art, such as through the use of radioisotopes, fluorescence, or a planar optical waveguide. See, for example, U.S. Pat. No. 4,868,105, WO 95/33197, and WO 95/33198, all of which are incorporated herein by reference.

The present invention lends itself readily to the preparation of "kits" containing the elements necessary to carry out the process. Such a kit may comprise a carrier being compartmentalized to receive in close confinement therein one or more containers, such as tubes or vials. One of the containers may contain unlabeled or detectably labeled DNA primers or probes, which may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers. Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used for isolating ITS sequences, selecting suitable primer sequences, testing primers for selective and diagnostic efficacy, and using such primers for disease and fungal isolate detection. The examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory Manual,* Cold Spring Harbor laboratory, Cold Spring Harbor, N.Y. (1989) and by T. J. Silhavy, M. L. Berman, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

Example 1

Fungal Isolates and Genomic Fungal DNA Extraction

See Table 1 for a listing of the fungal isolates used and their source. Fungi were grown in 150 ml potato dextrose broth inoculated with mycelial fragments from PDA (Potato Dextrose Agar) cultures. Cultures were incubated on an orbital shaker at 28° C. for 7–11 days. Alternatively, mycelia may be isolated directly from a PDA plate. Mycelia were pelleted by centrifugation and then ground in liquid nitrogen, and total genomic DNA was extracted using the protocol of Lee and Taylor (1990; In: PCR *Protocols: A Guide to Methods and Applications;* Eds.: Innes et al.; pages 282–287).

TABLE 1

Source of Test Isolates

| Isolate | Organism | Source | Origin |
|---|---|---|---|
| 6715 | *Pyrenophora tritici-repentis* | ATCC[1] | — |
| 44184 | *Pyrenophora tritici-repentis* | ATCC[1] | Australia |
| 205 | *Pyrenophora tritici-repentis* | Novartis[2] | Västerås, Sweden |
| 109 | *Pyrenophora tritici-repentis* | Novartis[2] | Vallskog, Sweden |
| 403 | *Pyrenophora tritici-repentis* | Novartis[2] | Vattholma, Sweden |
| 223 | *Pyrenophora tritici-repentis* | Novartis[2] | Västerås, Sweden |
| 407 | *Pyrenophora tritici-repentis* | Novartis[2] | Vattholma, Sweden |
| 1316 | *Pyrenophora tritici-repentis* | Novartis[2] | Vallskog, Sweden |
| PTR 3B | *Pyrenophora tritici-repentis* | L. Francl[3] | North Dakota |
| PTR 4A | *Pyrenophora tritici-repentis* | L. Francl[3] | North Dakota |
| PTR 1 | *Pyrenophora tritici-repentis* | L. Francl[3] | North Dakota |
| 148-1-1 | *Pyrenophora tritici-repentis* | L. Francl[3] | North Dakota |
| 119-2-3 | *Pyrenophora tritici-repentis* | L. Francl[3] | North Dakota |
| 83-A-3-1 | *Pyrenophora tritici-repentis* | L. Francl[3] | North Dakota |
| DL22 | *Pyrenophora tritici-repentis* | L. Francl[3] | Minnesota |
| 36570 | *Pyrenophora teres f. teres* | ATCC[1] | Denmark |
| 11404 | *Drechslera sorokiniana* | ATCC[1] | Minnesota |
| 44234 | *Rhizoctonia cerealis* | ATCC[1] | Netherlands |
| R-9420 | *Fusarium graminearum* | P. Nelson[4] | Washington |
| 62215 | *Fusarium culmorum* | ATCC[1] | Switzerland |
| 18222 | *Microdochium nivale* | ATCC[1] | Scotland |
| 44643 | *Pseudocercosporella herpotrichoides*-W type | ATCC[1] | Germany |
| 308 | *Pseudocercosporella herpotrichoides*-R type | Novartis[5] | — |
| 24425 | *Septoria nodorum* | ATCC[1] | Montana |
| 26517 | *Septoria tritici* | ATCC[1] | Minnesota |

TABLE 1-continued

Source of Test Isolates

| Isolate | Organism | Source | Origin |
| --- | --- | --- | --- |
| 60531 | *Cladosporium herbarum* | ATCC[1] | New Zealand |
| 52476 | *Cercospora arachidicola* | ATCC[1] | Oklahoma |
| HS-1 | *Helminthosporium sativum* | Novartis[2] | Sweden |
| DT-1 | *Pyrenophora teres* | Novartis[2] | Sweden |
| DR-1 | *Pyrenophora tritici-repentis* | Novartis[2] | Sweden |

[1]American Type Culture Collection, Rockville, Maryland, USA
[2]Novartis Sweden AB, 261 23 Landskrona, Sweden
[3]Dr. Len Francl, North Dakota State University, Fargo, North Dakota, USA
[4]Dr. Paul Nelson, Penn State University, State College, Pennsylvania, USA
[5]Novartis Crop Protection Limited, Basel, Switzerland

Example 2
Isolation of the Internal Transcribed Spacer (ITS) Regions

Approximately 600-bp long internal transcribed spacer (ITS) region fragments were PCR-amplified from 10 ng of genomic DNA isolated from *P. tritici-repentis* isolates 6715, 119-2-3, DL22, PTR4A, 44184, 205, 403, 109, 407, 1316, 223 and *P. teres* isolate 36570 using 50 pmol of primers ITS1 (5'-TCCGTAGGTGAACCTGCGG-3'; SEQ ID NO:1) and ITS4 (5'-TCCTCCGCTTATTGATATGC-3'; SEQ ID NO:4). PCRs were performed as described in Example 4. The ITS PCR products were cloned using the Invitrogen Corporation's (San Diego, Calif.) TA Cloning Kit (part no. K2000-01) using the PCR2.1 cloning vector. The DNA sequences of the ITS regions were determined by the dideoxy method using the Applied Biosystems (Foster City, Calif.) automated sequencer with the primers ITS1 (SEQ ID NO:1), ITS2 (5'-GCTGCGTTCTTCATCGATGC-3'; SEQ ID NO:2), ITS4 (SEQ ID NO:4) and the M13 universal -20 (5'-GTAAAACGACGGCCAGT-3'; SEQ ID NO:5) and Reverse (5'-AACAGCTATGACCATG-3'; SEQ ID NO:6) primers. The ITS primers ITS1, ITS2, ITS3, and ITS4 are detailed in White et al. (1990; In: PCR Protocols; Eds.: Innes et al. pages 315–322)

Example 3
DNA Extraction from Wheat

DNA was extracted from wheat using a bulk maceration method. The bulk maceration method was used to isolate DNA from several naturally infected wheat leaves from the field to optimize the field sampling method for high throughput analysis.

The following is the protocol for the bulk maceration method:

(1) Place the appropriate number of wheat leaves in a Bioreba (Reinach, Switzerland) heavy duty plastic bag (cat#490100). Weigh the plant tissue, plastic bag with leaves minus the tare (weight of the plastic bag).

(2) Add an equal volume (ml) of Muller Extraction Buffer (0.1% w/v Tween-80; 0.04 M Tris-Cl, pH 7.7; 0.15 M NaCl; 0.1% w/v BSA-Pentex fraction V; 0.01% w/v sodium azide; 200 mM EDTA) per weight (g) of wheat tissue. Macerate the tissue using a Bioreba Homex 6 homogenizer set at 70. Grind the leaves until the tissue is fibrous.

(3) Pool the extracts from multiple bags, if used, and vortex well. Aliquot the extraction juice into eppendorf tubes on ice.

(a) Boil 100 μl of the concentrated extract for 5 minutes.

(b) Place the boiled extract on ice.

(c) Make a 1:10 dilution by adding 10 μl from the boiled, concentrated extract to 90 μl of sterile dH$_2$O.

(d) Store the diluted extracts on ice until ready to use.

Example 4
Polymerase Chain Reaction Amplification

Polymerase chain reactions were performed with the GeneAmp Kit from Perkin-Elmer/Cetus (Norwalk, Conn.; part no. N808–0009) using 50 mM KCl, 2.5 mM MgCl$_2$, 10 mM Tris-HCl, pH8.3, containing 200 μM of each dTTP, dATP, dCTP, and dGTP, 50 pmol each primer, 2.5 units of Taq polymerase and 10 ng of genomic DNA or 1 μl of 1:10 diluted plant extract in a final volume of 50 μl. Reactions were run for 30–40 cycles of 15 s at 94° C.; 15 s at 50° C.–70° C.; and 45 s at 72° C. in a Perkin-Elmer/Cetus Model 9600 thermal cycler. The products were analyzed by loading 10 μl of each PCR sample on a 1.0% agarose gel and electrophoresing.

Example 5
Synthesis and Purification of Oligonucleotides

Oligonucleotides (primers) may be synthesized by, for example, either Integrated DNA Technologies (Coralville, Iowa) or Midland Certified Reagent Company (Midland, Tex).

Example 6
Selection of Species-Specific Primers

The ITS regions from the mulitiple isolates of *P. tritici-repentis* and the single isolate of *P. teres* were aligned. The oligonucleotide primers shown below in Table 2 were synthesized according to Example 5 based on analysis of the aligned sequences. Primers were designed to the regions that contain the greatest differences in sequence among the fungal species. Primers were also designed to regions highly conserved among the species in attempts to develop genus-specific primers. In addition, the published ribosomal gene-specific primers ITS1, ITS2, ITS3 and ITS4 (White et al., 1990; In: PCR Protocols; Eds.: Innes et al. pages 315–322) are synthesized for testing in combination with the primers specific for the ITS regions.

TABLE 2

Primers Designed for Fungal Detection

| Primer Template | Primer | Primer Sequence | |
|---|---|---|---|
| 18S rDNA | ITS1 | 5'-TCCGTAGGTGAACCTGCGG-3' | (SEQ ID NO:1) |
| 5.8S rDNA | ITS2 | 5'-GCTGCGTTCTTCATCGATGC-3' | (SEQ ID NO:2) |
| 5.8S rDNA | ITS3 | 5'-GCATCGATGAAGAACGCAGC-3' | (SEQ ID NO:3) |
| 25S rDNA | ITS4 | 5'-TCCTCCGCTTATTGATATGC-3' | (SEQ ID NO:4) |
| P. tritici-repentis | JB629 | 5'-GTACTACTTGTTTCCTTGGCG-3' | (SEQ ID NO:7) |
| P. tritici-repentis | JB630 | 5'-TCAGTTGCAATCAGCGTCAG-3' | (SEQ ID NO:8) |
| P. tritici-repentis | JB631 | 5'-TGGACAAGAGCGCAAATAATG-3' | (SEQ ID NO:9) |
| P. tritici-repentis | JB632 | 5'-ATGAAGCCGGACTGGGATA-3' | (SEQ ID NO:10) |
| P. tritici-repentis | JB633 | 5'-ATGAAGCCGGACTGGGATAGGG-3' | (SEQ ID NO:11) |
| P. tritici-repentis | JB634 | 5'-CGCTGCCTTGCCCGTCTGGC-3' | (SEQ ID NO:12) |
| P. tritici-repentis | JB635 | 5'-CGCTGCCTTGCCCGTCT-3' | (SEQ ID NO:13) |
| P. tritici-repentis | JB636 | 5'-CATGGACGCGCGACCGC-3' | (SEQ ID NO:14) |
| P. tritici-repentis | JB637 | 5'-CATGGACGCGCGACCGCGGC-3' | (SEQ ID NO:15) |
| P. tritici-repentis | JB638 | 5'-CTCCGAAACCAGTAGGCC-3' | (SEQ ID NO:16) |
| P. tritici-repentis | JB651 | 5'-GATAGGGCCTCGCTGCCTTGC-3' | (SEQ ID NO:17) |
| P. tritici-repentis | JB652 | 5'-GATAGGGCCTCGCTGCCT-3' | (SEQ ID NO:18) |
| P. tritici-repentis | JB653 | 5'-AAGGTTGAAAGAAGCTTCATGG-3' | (SEQ ID NO:19) |
| P. tritici-repentis | JB654 | 5'-CAAAAGGTTGAAAGAAGCTTCATGG-3' | (SEQ ID NO:20) |
| P. tritici-repentis | JB655 | 5'-AAGCCGGACTGGGATAGG-3' | (SEQ ID NO:21) |
| P. tritici-repentis | JB656 | 5'-CAAAAGGTTGAAAGAAGC-3' | (SEQ ID NO:22) |
| P. tritici-repentis | JB657 | 5'-GCCGGACTGGGATAGGGC-3' | (SEQ ID NO:23) |
| P. tritici-repentis | JB658 | 5'-GGACTGGGATAGGGCCTC-3' | (SEQ ID NO:24) |
| P. tritici-repentis | JB659 | 5'-GAAGCTTCATGGACGCGCG-3' | (SEQ ID NO:25) |
| P. tritici-repentis | JB660 | 5'-GGCGAGTCTCGGGAGAGA-3' | (SEQ ID NO:26) |
| P. tritici-repentis | JB675 | 5'-GCCGGACTGGGATAGGGCCTC-3' | (SEQ ID NO:27) |
| P. tritici-repentis | JB676 | 5'-GGCGAGTCTCGGGAGAGAGAC-3' | (SEQ ID NO:28) |

Example 7
Determination of Primer Specificity to Purified Fungal Genomic DNA PCRs were performed according to Example 4 using different primer combinations (Table 3) in attempts to amplify single specific fragments. Specific PCR amplification products were produced from primers designed from the ITS regions between the 18S and 25S ribosomal DNA subunits of each fungal strain of interest.

TABLE 3

ITS-Derived Diagnostic PCR Primers

| Primer specificity | 5' Primer | 3' Primer | Approximate size of amplified fragment |
|---|---|---|---|
| P. tritici-repentis | JB629 (SEQ ID NO:7) | JB631 (SEQ ID NO:9) | 390 bp |
| P. tritici-repentis | JB633 (SEQ ID NO:11) | JB637 (SEQ ID NO:15) | 485 bp |
| P. tritici-repentis | JB629 (SEQ ID NO:7) | JB636 (SEQ ID NO:14) | 411 bp |

TABLE 3-continued

ITS-Derived Diagnostic PCR Primers

| Primer specificity | 5'Primer | 3'Primer | Approximate size of amplified fragment |
| --- | --- | --- | --- |
| P. teres<br>P. tritici-repentis | ITS1 (SEQ ID NO:1) | JB631 (SEQ ID NO:9) | 500 bp |
| P. tritici-repentis<br>D. sorokiniana | JB630 (SEQ ID NO:8) | ITS4 (SEQ ID NO:4) | 433 bp |
| P. tritici-repentis | JB651 (SEQ ID NO:17) | JB654 (SEQ ID NO:20) | 473 bp |
| P. tritici-repentis | JB652 (SEQ ID NO:18) | JB653 (SEQ ID NO:19) | 498 bp |
| P. tritici-repentis<br>P. teres | ITS1 (SEQ ID NO:1) | JB653 (SEQ ID NO:19) | 448 bp |
| P. tritici-repentis | JB629 (SEQ ID NO:7) | JB653 (SEQ ID NO:19) | 438 bp |
| P. tritici-repentis | JB630 (SEQ ID NO:8) | JB653 (SEQ ID NO:19) | 357 bp |
| P. tritici-repentis | JB632 (SEQ ID NO:10) | JB653 (SEQ ID NO:19) | 512 bp |
| P. tritici-repentis | JB635 (SEQ ID NO:13) | JB653 (SEQ ID NO:19) | 482 bp |
| P. tritici-repentis | JB657 (SEQ ID NO:23) | JB660 (SEQ ID NO:26) | 393 bp |
| P. tritici-repentis | JB657 (SBQ ID NO:23) | JB653 (SEQ ID NO:19) | 508 bp |
| P. tritici-repentis | JB658 (SEQ ID NO:24) | JB653 (SEQ ID NO:19) | 503 bp |
| P. tritici-repentis | JB675 (SEQ ID NO:27) | JB676 (SEQ ID NO:28) | 392 bp |

Example 8
Determination of Primer Specificity to Plant Tissue Infected with Fungi and Cross-Reactivity with Other Cereal Fungal Pathogens Total genomic DNA was isolated as described in Example 3 from healthy wheat leaves and from wheat leaves infected with *P. tritici-repentis*. PCRs were performed as described in Example 4 testing primer combinations listed in Table 3 against DNA from the wheat tissue. Purified fungal genomic DNAs were obtained as described in Example 1 and PCR assayed as described in Example 4 using the diagnostic primers. Other fungal DNA species and isolates were tested for the ability of the diagnostic primers to cross-react therewith. The results of these experiments are as follows:

*P. tritici-repentis* specific primer combination JB675 (SEQ ID NO:27) and JB676 (SEQ ID NO:28) amplified a 392 bp fragment from DNA from all of the *P. tritici-repentis* isolates listed in Table 1 and from *P. tritici-repentis*-infected wheat tissue. This primer combination did not amplify a diagnostic fragment from healthy wheat tissue nor from purified genomic DNA from the following common cereal pathogens listed in Table 1: *P. teres, R. cerealis, D. sorokiniana, F. graminearum, F. culmorum, M. nivale, P. herpotrichoides* R- and W-pathotypes, *S. nodorum, C. herbarum, S. tritici, C. arachidicola* and *H. sativum*. Similar diagnostic results were obtained with the following *P. tritici-repentis*-specific primer combinations: JB658 (SEQ ID NO:24) and 3B653 (SEQ ID NO:19);

1JB657 (SEQ ID NO:23) and JB653 (SEQ ID NO: 19); JB657 (SEQ ID NO:23) and JB660 -20 (SEQ ID NO:26); JB652 (SEQ ID NO:18) and 3B653 (SEQ ID NO:19); and 3B629 (SEQ NO:7) and 3B631 (SEQ ID NO:9). *P. tritici-repentis*-specific primers JB633 (SEQ ID NO: 1 1) and JB637 (SEQ ID NO: 15) produced similar results; however, this primer combination was not tested against *P. tritici-repentis*-infected wheat.

The primers JB651 (SEQ ID NO: 17) and JB654 (SEQ ID NO:20) amplified a 473 bp fragment from DNA from *P. tritici-repentis* isolates #6715 and #DL22. The primers amplified a smaller fragment, approximately 400 bp, from healthy wheat DNA. These primers did not amplify purified genomic DNA from the following common cereal pathogens listed in Table 1: *P. teres, R. cerealis, D. sorokiniana, F. graminearum, F. culmorum, M. nivale, P. herpotrichoides* R- and W-pathotypes, *S. nodorum, C. herbarum, S. tritici* and *C. arachidicola*.

Primer combination JB635 (SEQ ID NO:13) and JB653 (SEQ ID NO:19) amplified a 482 bp fragment; primer combination JB632 (SEQ ID NO:10) and JB653 (SEQ ID NO:19) amplified a 512 bp fragment; primer combination JB630 (SEQ ID NO:8) and JB653 (SEQ ID NO:19) amplified a 357 bp fragment; and primer combination JB629 (SEQ ID NO:7) and JB653 (SEQ ID NO:19) amplified a 438 bp fragment from DNA from *P. tritici-repentis* isolates #6715 and DL22. These primer combinations did not amplify any fragments from DNA from *D. sorokiniana* isolate #11404 and *P. teres* isolate #36570. Primer combination JB629 (SEQ ID NO:7) and JB636 (SEQ ID NO:14) amplified a 411 bp fragment from *P. tritici-repentis* isolate #6715 DNA, but did not amplify from DNA from *D. sorokiniana* #11404 and *S. nodorum* #24425. The primers JB630 (SEQ ID NO:8) and ITS4 (SEQ ID NO:4) amplified a 433 bp fragment from *P. tritici-repentis* isolate #6715 DNA and also from DNA from *D. sorokiniana* #11404, but did not amplify from DNA isolated from *S. nodorum* #24425 and *S. tritici* #26517.

Primer combination ITS1 (SEQ ID NO:1) and JB653 (SEQ ID NO:19) amplified a 448 bp fragment from DNA isolated from *P. tritici-repentis* and also from *P. teres*. This primer combination did not amplify a diagnostic fragment from healthy wheat tissue nor from purified genomic DNA from the following common cereal pathogens listed in Table 1: *R. cerealis, D. sorokiniana, F. graminearum, F. culmorum, M. nivale, P. herpotrichoides R-* and W-pathotypes, *S. nodorum, C. herbarum, S. tritici, C. arachidicola* and *H. sativum*. Similar diagnostic results were obtained with the primer combination ITS1 (SEQ ID NO:1) and JB631 (SEQ ID NO:9).

While the present invention has been described with reference to specific embodiments thereof, it will be appreciated that numerous variations, modifications, and further embodiments are possible, and accordingly, all such variations, modifications and embodiments are to be regarded as being within the scope of the present invention.

What is claimed is:

1. An isolated DNA molecule comprising a nucleotide sequence of nucleotides 1–517 of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41.

2. An Internal Transcribed Spacer sequence isolated from the ribosomal RNA gene region of *Pyrenophora tritici-repentis,* wherein said Internal Transcribed Spacer sequence is selected from the group consisting of: nucleotides 31–208 of SEQ ID NO:29; nucleotides 366–526 of SEQ ID NO:29; nucleotides 31–208 of SEQ ID NO:30; nucleotides 366–526 of SEQ ID NO:30; nucleotides 31–208 of SEQ ID NO:31;

nucleotides 366–526 of SEQ ID NO:31; nucleotides 31–208 of SEQ ID NO:32; nucleotides 366–526 of SEQ ID NO:32; nucleotides 31–208 of SEQ ID NO:33; nucleotides 366–527 of SEQ ID NO:33; nucleotides 31–208 of SEQ ID NO:34; nucleotides 366–526 of SEQ ID NO:34; nucleotides 31–208 of SEQ ID NO:35; nucleotides 366–527 of SEQ ID NO:35; nucleotides 31–208 of SEQ ID NO:36; nucleotides 366–526 of SEQ ID NO:36; nucleotides 31–209 of SEQ ID NO:37; nucleotides 367–527 of SEQ ID NO:37; nucleotides 31–208 of SEQ ID NO:38; nucleotides 366–526 of SEQ ID NO:38; nucleotides 31–208 of SEQ ID NO:39; nucleotides 368–534 of SEQ ID NO:39; nucleotides 31–208 of SEQ ID NO:40; and nucleotides 366–527 of SEQ ID NO:40.

3. A method for detecting *Pyrenophora tritici-repentis,* comprising the steps of:
   (a) designing at least one PCR primer comprising an at least 10 contiguous nucleotide portion identical in sequence to an at least 10 contiguous nucleotide portion of a nucleotide sequence of claim 2;
   (b) isolating DNA from plant tissue infected with *Pyrenophora tritici-repentis;*
   (c) subjecting the DNA of step (b) to polymerase chain reaction amplification using the primer or primers of step (a); and
   (d) detecting *Pyrenophora tritici-repentis* by visualizing the product or products of the polymerase chain reaction amplification of step (c).

4. An oligonucleotide primer comprising an at least 10 contiguous nucleotide portion identical in sequence to an at least 10 contiguous nucleotide portion of a sequence selected from the group consisting of: nucleotides 31–208 of SEQ ID NO:29; nucleotides 366–517 of SEQ ID NO:29; nucleotides 31–208 of SEQ ID NO:30; nucleotides 366–526 of SEQ ID NO:30; nucleotides 31–208 of SEQ ID NO:31; nucleotides 366–526 of SEQ ID NO:31; nucleotides 31–208 of SEQ ID NO:32; nucleotides 366–526 of SEQ ID NO:32; nucleotides 31–208 of SEQ ID NO:33; nucleotides 366–527 of SEQ ID NO:33; nucleotides 31–208 of SEQ ID NO:34; nucleotides 366–526 of SEQ ID NO:34; nucleotides 31–208 of SEQ ID NO:35; nucleotides 366–527 of SEQ ID NO:35; nucleotides 31–208 of SEQ ID NO:36; nucleotides 366–526 of SEQ ID NO:36; nucleotides 31–209 of SEQ ID NO:37; nucleotides 367–527 of SEQ ID NO:37; nucleotides 31–208 of SEQ ID NO:38; nucleotides 366–526 of SEQ ID NO:38; nucleotides 31–208 of SEQ ID NO:39; nucleotides 368–534 of SEQ ID NO:39; nucleotides 31–208 of SEQ ID NO:40; and nucleotides 366–527 of SEQ ID NO:40 wherein said primer specifically detects and amplifies *Pyrenophora tritici-repentis.*

5. A pair of oligonucleotide primers for use in the amplification-based detection of a fungal Internal Transcribed Spacer DNA sequence, wherein at least one of said primers is the oligonucleotide primer of claim 4.

6. A diagnostic kit used in detecting a fungal pathogen, comprising at least one primer according to claim 4.

7. A method for the detection of a fungal pathogen, comprising the steps of:
   (a) isolating DNA from a plant leaf infected with a fungal pathogen;
   (b) subjecting said DNA to polymerase chain reaction amplification using at least one primer comprising an at least 10 contiguous nucleotide portion identical in sequence to an at least 10 contiguous nucleotide portion of the sequence of claim 2; and
   (c) detecting said fungal pathogen by visualizing the product or products of said polymerase chain reaction amplification.

8. The method of claim 7, wherein said fungal pathogen is *Pyrenophora tritici-repentis.*

9. The method of claim 7, wherein said fungal pathogen is *Pyrenophora teres.*

10. The method of claim 7, wherein said fungal pathogen is *Drechslera sorokiniana.*

11. A method for detecting *Pyrenophora tritici-repentis,* comprising the steps of:
   (a) designing at least one PCR primer comprising an at least 10 contiguous nucleotide portion identical in sequence to an at least 10 contiguous nucleotide portion of the Internal Transcribed Spacer sequence of claim 2;
   (b) isolating DNA from plant tissue infected with *Pyrenophoria tritici-repentis*
   (c) subjecting the DNA of step (b) to polymerase chain reaction amplification using the primer or primers of step (a); and
   (d) detecting *Pyrenophora tritici-repentis* by visualizing the product or products of the polymerase chain reaction amplification of step (c).

12. A method for detecting *Pyrenophora tritici-repentis,* comprising the steps of:
   (a) designing at least one polynucleotide label probe comprising:
      (i) a nucleic acid region having a sequence that is fully complementary to at least 10 contiguous nucleotides of the Internal Transcribed Spacer sequence of claim 2, and
      (ii) a label portion comprising either a label that provides a signal when said probe hybridizes with another nucleic acid molecule, or a binding site for said label;
   (b) isolating DNA from plant tissue infected with *Pyrenophora tritici-repentis*
   (c) hybridizing the DNA of stop (b) with the probe or probes of step (a); and
   (d) detecting *Pyrenophora tritici-repentis* by detecting the label, wherein detection of the label indicates that the hybridization of step (c) has occurred.

13. An oligonucleotide primer for use in the amplification-based detection of a fungal Internal Transcribed Spacer DNA sequence, wherein said primer is selected from the group consisting of SEQ ID NOs:7–28.

14. A pair of oligonucleotide primers for use in the amplification-based detection of a fungal Internal Transcribed Spacer DNA sequence, wherein at least one of said primers is the oligonucleotide primer of claim 13.

15. A pair of oligonucleotide primers according to claim 14, wherein said pair is selected from the following primer pairs:

SEQ ID NO:7 and SEQ ID NO:9;
SEQ ID NO:11 and SEQ ID NO:15;
SEQ ID NO:7 and SEQ ID NO:14;
SEQ ID NO:1 and SEQ ID NO:9;
SEQ ID NO:8 and SEQ ID NO:4;
SEQ ID NO:17 and SEQ ID NO:20;
SEQ ID NO:18 and SEQ ID NO:19;
SEQ ID NO:1 and SEQ ID NO:19;
SEQ ID NO:7 and SEQ ID NO:19;
SEQ ID NO:8 and SEQ ID NO:19;
SEQ ID NO:10 and SEQ ID NO:19;
SEQ ID NO:13 and SEQ ID NO:19;
SEQ ID NO:23 and SEQ ID NO:26;

SEQ ID NO:23 and SEQ ID NO:19;
SEQ ID NO:24 and SEQ ID NO:19; and
SEQ ID NO:27 and SEQ ID NO:28.

16. A method for detecting *Pyrenophora tritici-repentis*, comprising the steps of:
   (a) isolating DNA from a plant leaf infected with *Pyrenophora tritici-repentis*;
   (b) amplifying a part of the Internal Transcribed Spacer sequence of *Pyrenophora tritici-repentis* using said DNA as a template in a polymerase chain reaction with a pair of oligonucleotide primers according to claim 15; and
   (c) detecting *Pyrenophora tritici-repentis* by visualizing the amplified part of the Internal Transcribed Spacer sequence.

17. A pair of oligonucleotide primers according to claim 15, wherein said pair is either
SEQ ID NO:1 and SEQ ID NO:9 or
SEQ ID NO:1 and SEQ ID NO:19.

18. A method for detecting *Pyrenophora teres*, comprising the steps of:
   (a) isolating DNA from a plant leaf infected with *Pyrenophora teres*;
   (b) amplifying a part of the Internal Transcribed Spacer sequence of *Pyrenophora teres* using said DNA as a template in a polymerase chain reaction with a pair of oligonucleotide primers according to claim 17; and
   (c) detecting *Pyrenophora teres* by visualizing the amplified part of the Internal Transcribed Spacer sequence.

19. A pair of oligonucleotide primers according to claim 15, wherein said pair is SEQ ID NO:8 and SEQ ID NO:4.

20. A method for detecting *Drechslera sorokiniana*, comprising the steps of:
   (a) isolating DNA from a plant leaf infected with *Drechslera sorokiniana*;
   (b) amplifying a part of the Internal Transcribed Spacer sequence of *Drechslera sorokiniana* using said DNA as a template in a polymerase chain reaction with a pair of oligonucleotide primers according to claim 19; and
   (c) detecting *Drechslera sorokiniana* by visualizing the amplified part of the Internal Transcribed Spacer sequence.

* * * * *

```
                            SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer ITS1"

(xi) SEQUENCE DESCRIPTION: SEQ ID NO:1:

TCCGTAGGTG AACCTGCGG                                                    19

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer ITS2"

(xi) SEQUENCE DESCRIPTION: SEQ ID NO:2:

GCTGCGTTCT TCATCGATGC                                                   20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer ITS3"

(xi) SEQUENCE DESCRIPTION: SEQ ID NO:3:

GCATCGATGA AGAACGCAGC                                                   20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer ITS4"

(xi) SEQUENCE DESCRIPTION: SEQ ID NO:4:
```

```
TCCTCCGCTT ATTGATATGC                                              20
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "M13 Universal-20 Primer"

(xi) SEQUENCE DESCRIPTION: SEQ ID NO:5:

```
GTAAAACGAC GGCCAGT                                                 17
```

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Reverse Primer used in
            Example 2"

(xi) SEQUENCE DESCRIPTION: SEQ ID NO:6:

```
AACAGCTATG ACCATG                                                  16
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB629"

(xi) SEQUENCE DESCRIPTION: SEQ ID NO:7:

```
GTACTACTTG TTTCCTTGGC G                                            21
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB630"

(xi) SEQUENCE DESCRIPTION: SEQ ID NO:8:

```
TCAGTTGCAA TCAGCGTCAG                                              20
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB31"

(xi) SEQUENCE DESCRIPTION: SEQ ID NO:9:

TGGACAAGAG CGCAAATAAT G                                             21

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB632"

(xi) SEQUENCE DESCRIPTION: SEQ ID NO:10:

ATGAAGCCGG ACTGGGATA                                                19

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB633"

(xi) SEQUENCE DESCRIPTION: SEQ ID NO:11:

ATGAAGCCGG ACTGGGATAG GG                                            22

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB634"

(xi) SEQUENCE DESCRIPTION: SEQ ID NO:12:

CGCTGCCTTG CCCGTCTGGC                                               20

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB635"

(xi) SEQUENCE DESCRIPTION: SEQ ID NO:13:

CGCTGCCTTG CCCGTCT                                                  17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer JB636"

(xi) SEQUENCE DESCRIPTION: SEQ ID NO:14:

CATGGACGCG CGACCGC                                                          17

(2) INFORMATION FOR SEQ ID NO:15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer JB637"

(xi) SEQUENCE DESCRIPTION: SEQ ID NO:15:

CATGGACGCG CGACCGCGGC                                                       20

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer JB638"

(xi) SEQUENCE DESCRIPTION: SEQ ID NO:16:

CTCCGAAACC AGTAGGCC                                                         18

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer JB651"

(xi) SEQUENCE DESCRIPTION: SEQ ID NO:17:

GATAGGGCCT CGCTGCCTTG C                                                     21

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer JB652"

(xi) SEQUENCE DESCRIPTION: SEQ ID NO:18:

GATAGGGCCT CGCTGCCT                                                         18

(2) INFORMATION FOR SEQ ID NO:19:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (A) DESCRIPTION: /desc = "Primer JB653"

(xi) SEQUENCE DESCRIPTION: SEQ ID NO:19:

AAGGTTGAAA GAAGCTTCAT GG                                                    22

(2) INFORMATION FOR SEQ ID NO:20:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer JB654"

(xi) SEQUENCE DESCRIPTION: SEQ ID NO:20:

CAAAAGGTTG AAAGAAGCTT CATGG                                                 25

(2) INFORMATION FOR SEQ ID NO:21:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer JB655"

(xi) SEQUENCE DESCRIPTION: SEQ ID NO:21:

AAGCCGGACT GGGATAGG                                                         18

(2) INFORMATION FOR SEQ ID NO:22:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer JB656"

(xi) SEQUENCE DESCRIPTION: SEQ ID NO:22:

CAAAAGGTTG AAAGAAGC                                                         18

(2) INFORMATION FOR SEQ ID NO:23:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer JB657"

(xi) SEQUENCE DESCRIPTION: SEQ ID NO:23:

GCCGGACTGG GATAGGGC                                                         18

(2) INFORMATION FOR SEQ ID NO:24:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer JB658"

(xi) SEQUENCE DESCRIPTION: SEQ ID NO:24:

GGACTGGGAT AGGGCCTC                                                    18

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer JB659"

(xi) SEQUENCE DESCRIPTION: SEQ ID NO:25:

GAAGCTTCAT GGACGCGCG                                                   19

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer JB660"

(xi) SEQUENCE DESCRIPTION: SEQ ID NO:26:

GGCGAGTCTC GGGAGAGA                                                    18

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer JB675"

(xi) SEQUENCE DESCRIPTION: SEQ ID NO:27:

GCCGGACTGG GATAGGGCCT C                                                21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer JB676"

(xi) SEQUENCE DESCRIPTION: SEQ ID NO:28:

GGCGAGTCTC GGGAGAGAGA C                                                21

(2) INFORMATION FOR SEQ ID NO:29:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: Pyrenophora tritici-repentis
    (C) INDIVIDUAL ISOLATE: consensus sequence (ix) FEATURE:
    (A) NAME/KEY: misc_feature
    (B) LOCATION: 1..30
    (D) OTHER INFORMATION: /note= "3' end of small subunit rRNA gene"

(ix) FEATURE:
    (A) NAME/KEY: misc_feature
    (B) LOCATION: 31..208
    (D) OTHER INFORMATION: /note= "ITS1"

(ix) FEATURE:
    (A) NAME/KEY: misc_feature
    (B) LOCATION: 209..365
    (D) OTHER INFORMATION: /note= "5.8S rRNA gene"

(ix) FEATURE:
    (A) NAME/KEY: misc_feature
    (B) LOCATION: 366..526
    (D) OTHER INFORMATION: /note= "ITS2"

(ix) FEATURE:
    (A) NAME/KEY: misc_feature
    (B) LOCATION: 527..579
    (D) OTHER INFORMATION: /note= "5' end of large subunit rRNA gene"

(xi) SEQUENCE DESCRIPTION: SEQ ID NO:29:

```
TCCGTAGGTG AACCTGCGGA GGGATCATTA CACAAATATG AAGCCGGACT GGGATAGGGC    60

CTCGCTGCCT TGCCCGTCTG GCGCCATATT CACCCATGTC TTTTTGCGTA CTACTTGTTT   120

CCTTGGCGGG TCCGCCCGCC AATTGGACCT TATTCAAACC TTTTTTTCAG TTGCAATCAG   180

CGTCAGCAAA ACAAATGTAA TCAATTACAA CTTTCAACAA CGGATCTCTT GGTTCTGGCA   240

TCGATGAAGA ACGCAGCGAA ATGCGATAAG TAGTGTGAAT TGCAGAATTC AGTGAATCAT   300

CGAATCTTTG AACGCACATT GCGCCCTTTG GTATTCCAAA GGGCATGCCT GTTCGAGCGT   360

CATTTGTACC CTCAAGCTTT GCTTGGTGTT GGGCGTCTTG TCTCTCTCCC GAGACTCGCC   420

TTAAAATCAT TGGCAGCCGG CCTACTGGTT TCGGAGCGCA GCACATTATT TGCGCTCTTG   480

TCCAGCCGCG GTCGCGCGTC CATGAAGCTT CTTTCAACCT TTTGACCTCG GATCAGGTAG   540

GGATACCCGC TGAACTTAAG CATATCAATA AGCGGAGGA                          579
```

(2) INFORMATION FOR SEQ ID NO:30:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: 6715

(vii) IMMEDIATE SOURCE:
        (B) CLONE: 2 and 4 (consensus)

(ix) FEATURE:
        (A) NAME/KEY: misc_feature
        (B) LOCATION: 1..30
        (D) OTHER INFORMATION: /note= "3' end of small subunit rRNA gene"

(ix) FEATURE:
              (A) NAME/KEY: misc_feature
              (B) LOCATION: 31..208
              (D) OTHER INFORMATION: /note= "ITS1"

(ix) FEATURE:
              (A) NAME/KEY: misc_feature
              (B) LOCATION: 209..365
              (D) OTHER INFORMATION: /note= "5.8S rRNA gene"

(ix) FEATURE:
              (A) NAME/KEY: misc_feature
              (B) LOCATION: 366..526
              (D) OTHER INFORMATION: /note= "ITS2"

(ix) FEATURE:
              (A) NAME/KEY: misc_feature
              (B) LOCATION: 527..579
              (D) OTHER INFORMATION: /note= "5' end of large subunit
                    rRNA gene"

(xi) SEQUENCE DESCRIPTION: SEQ ID NO:30:

TCCGTAGGTG AACCTGCGGA GGGATCATTA CACAAATATG AAGCCGGACT GGGATAGGGC      60

CTCGCTGCCT TGCCCGTCTG GCGCCATATT CACCCATGTC TTTTTGCGTA CTACTTGTTT     120

CCTTGGCGGG TCCGCCCGCC AATTGGACCT TATTCAAACC TTTTTTTCAG TTGCAATCAG     180

CGTCAGCAAA ACAAATGTAA TCAATTACAA CTTTCAACAA CGGATCTCTT GGTTCTGGCA     240

TCGATGAAGA ACGCAGCGAA ATGCGATAAG TAGTGTGAAT TGCAGAATTC AGTGAATCAT     300

CGAATCTTTG AACGCACATT GCGCCCTTTG GTATTCCAAA GGGCATGCCT GTTCGAGCGT     360

CATTTGTACC CTCAAGCTTT GCTTGGTGTT GGGCGTCTTG TCTCTCTCCC GAGACTCGCC     420

TTAAAATCAT TGGCAGCCGG CCTACTGGTT TCGGAGCGCA GCACATTATT TGCGCTCTTG     480

TCCAGCCGCG GTCGCGCGTC CATGAAGCTT CTTTCAACCT TTTGACCTCG GATCAGGTAG     540

GGATACCCGC TGAACTTAAG CATATCAATA AGCGGAGGA                            579

(2) INFORMATION FOR SEQ ID NO:31:

(i) SEQUENCE CHARACTERISTICS:
              (A) LENGTH: 579 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: Pyrenophora tritici-repentis
              (C) INDIVIDUAL ISOLATE: 119-2-3

(vii) IMMEDIATE SOURCE:
              (B) CLONE: 2-2

(ix) FEATURE:
              (A) NAME/KEY: misc_feature
              (B) LOCATION: 1..30
              (D) OTHER INFORMATION: /note= "3' end of small subunit
                    rRNA gene"

(ix) FEATURE:
              (A) NAME/KEY: misc_feature
              (B) LOCATION: 31..208
              (D) OTHER INFORMATION: /note= "ITS1"

(ix) FEATURE:
              (A) NAME/KEY: misc_feature
              (B) LOCATION: 209..365
              (D) OTHER INFORMATION: /note= "5.8S rRNA gene"

(ix) FEATURE:

```
        (A) NAME/KEY: misc_feature
        (B) LOCATION: 366..526
        (D) OTHER INFORMATION: /note= "ITS2"

(ix) FEATURE:
        (A) NAME/KEY: misc_feature
        (B) LOCATION: 527..579
        (D) OTHER INFORMATION: /note= "5' end of large subunit
            rRNA gene"

(xi) SEQUENCE DESCRIPTION: SEQ ID NO:31:

TCCGTAGGTG AACCTGCGGA GGGATCATTA CACAAATATG AAGCCGGACT GGGATAGGGC    60

CTCGCTGCCT TGCCCGTCTG GCGCCATATT CACCCATGTC TTTTTGCGTA CTACTTGTTT   120

CCTTGGCGGG TCCGCCCGCC AATTGGACCT TATTCAAACC TTTTTTTCAG TTGCAATCAG   180

CGTCAGCAAA ACAAATGTAA TCAATTACAA CTTTCAACAA CGGATCTCTT GGTTCTGGCA   240

TCGATGAAGA ACGCAGCGAA ATGCGATAAG TAGTGTGAAT TGCAGAATTC AGTGAATCAT   300

CGAATCTTTG AACGCACATT GCGCCCTTTG GTATTCCAAA GGGCATGCCT GTTCGAGCGT   360

CATTTGTACC CTCAAGCTTT GCTTGGTGTT GGGCGTCTTG TCTCTCTCCC GAGACTCGCC   420

TTAAAATCAT TGGCAGCCGG CCTACTGGTT TCGGARCGCA RCACATTATT TGCGCTCTTG   480

TCCAGCCGCG GTCGCGCGTC CATGAAGCTT CTTTCAACCT TTTGACCTCG GATCAGGTAG   540

GGATACCCGC CGAACTTAAG CATATCAATA AGCGGAGGA                          579

(2) INFORMATION FOR SEQ ID NO:32:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: DL22

(vii) IMMEDIATE SOURCE:
        (B) CLONE: 1-1

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..208
        (D) OTHER INFORMATION: /note= "ITS1"

(ix) FEATURE:
        (A) NAME/KEY: misc_feature
        (B) LOCATION: 209..365
        (D) OTHER INFORMATION: /note= "5.8S rRNA gene"

(ix) FEATURE:
        (A) NAME/KEY: misc_feature
        (B) LOCATION: 366..526
        (D) OTHER INFORMATION: /note= "ITS2"

(ix) FEATURE:
        (A) NAME/KEY: misc_feature
        (B) LOCATION: 527..579
        (D) OTHER INFORMATION: /note= "5' end of large subunit
            rRNA gene"

(xi) SEQUENCE DESCRIPTION: SEQ ID NO:32:
```

```
TCCGTAGGTG AACCTGCGGA GGGATCATTA CACAAATATG AAGCCGGACT GGGATAGGGC      60

CTCGCTGCCT TGCCCGTCTG GCGCCATATT CACCCATGTC TTTTTGCGTA CTACTTGTTT     120

CCTTGGCGGG TCCGCCCGCC AATTGGACCT TATTCAAACC TTTTTTTCAG TTGCAATCAG     180

CGTCAGCAAA ACAAATGTAA TCAATTACAA CTTTCAACAA CGGATCTCTT GGTTCTGGCA     240

TCGATGAAGA ACGCAGCGAA ATGCGATAAG TAGTGTGAAT TGCAGAATTC AGTGAATCAT     300

CGAATCTTTG AACGCACATT GCGCCCTTTG GTATTCCAAA GGGCATGCCT GTTCGAGCGT     360

CATTTGTACC CTCAAGCTTT GCTTGGTGTT GGGCGTCTTG TCTCTCTCCC GARACTCGCC     420

TTAAAATCAT TGGCAGCCGG CCTACTGGTT TCGGARCGCA GCACATTATT TGCGCTCTTG     480

TCCAGCCGCG GTCGCGCGTC CATGAAGCTT CTTTCAACCT TTTGACCTCG GATCAGGTAG     540

GGATACCCGC TGAACTTAAG CATATCAATA AGCGGAGGA                            579
```

(2) INFORMATION FOR SEQ ID NO:33:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: PTR4A (vii) IMMEDIATE SOURCE:
        (B) CLONE: 2-3

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..208
        (D) OTHER INFORMATION: /note= "ITS1"

(ix) FEATURE:
        (A) NAME/KEY: misc_feature
        (B) LOCATION: 209..365
        (D) OTHER INFORMATION: /note= "5.8S rRNA gene"

(ix) FEATURE:
        (A) NAME/KEY: misc_feature
        (B) LOCATION: 366..527
        (D) OTHER INFORMATION: /note= "ITS2"

(ix) FEATURE:
        (A) NAME/KEY: misc_feature
        (B) LOCATION: 528..580
        (D) OTHER INFORMATION: /note= "5' end of large subunit
            rRNA gene"

(xi) SEQUENCE DESCRIPTION: SEQ ID NO:33:

```
TCCGTAGGTG AACCTGCGGA GGGATCATTA CACAAATATG AAGCCGGACT GGGATAGGGC      60

CTCGCTGCCT TGCCCGTCTG GCGCCATATT CACCCATGTC TTTTTGCGTA CTACTTGTTT     120

CCTTGGCGGG TCCGCCCGCC AATTGGACCT TATTCAAACC TTTTTTTCAG TTGCAATCAG     180

CGTCAGCAAA ACAAATGTAA TCAATTACAA CTTTCAACAA CGGATCTCTT GGTTCTGGCA     240

TCGATGAAGA ACGCAGCGAA ATGCGATAAG TAGTGTGAAT TGCAGGATTC AGTGAATCAT     300

CGAATCTTTG AACGCACATT GCGCCCTTTG GTATTCCAAA GGGCATGCCT GTTCGAGCGA     360
```

| | |
|---|---|
| CATTTGTACC CTCAAGCTTT GCTTGGTGTT GGGCGTCTTG TCTCTCTCCC NRARACTCGC | 420 |
| CTTAAAAWCM TTGGCMRCCG GCCTACTGGT TTCSGAGMGC AGCACATTAT TTGCGCTCTT | 480 |
| GTCCAGCCGC GGTCGCGCGT CCATGAAGCT TCTTTCAACC TTTTGACCTC GGATCAGGTA | 540 |
| GGGATACCCG CTGAACTTAA GCATATCAAT AAGCGGAGGA | 580 |

(2) INFORMATION FOR SEQ ID NO:34:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: 44184

(vii) IMMEDIATE SOURCE:
        (B) CLONE: 3-1

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..208
        (D) OTHER INFORMATION: /note= "ITS1"

(ix) FEATURE:
        (A) NAME/KEY: misc_feature
        (B) LOCATION: 209..365
        (D) OTHER INFORMATION: /note= "5.8S rRNA gene"

(ix) FEATURE:
        (A) NAME/KEY: misc_feature
        (B) LOCATION: 366..526
        (D) OTHER INFORMATION: /note= "ITS2"

(ix) FEATURE:
        (A) NAME/KEY: misc_feature
        (B) LOCATION: 527..579
        (D) OTHER INFORMATION: /note= "5' end of large subunit
            rRNA gene"

(xi) SEQUENCE DESCRIPTION: SEQ ID NO:34:

| | |
|---|---|
| TCCGTAGGTG AACCTGCGGA GGGATCATTA CACAAATATG AAGCCGGACT GGGATAGGGC | 60 |
| CTCGCTGCCT TGCCCGTCTG GCGCCATATT CACCCATGTC TTTTTGCGTA CTACTTGTTT | 120 |
| CCTTGGCGGG TCCGCCCGCC AATTGGACCT TATTCAAACC TTTTTTTCAG TTGCAATCAG | 180 |
| CGTCAGCAAA ACAAATGTAA TCAATTACAA CTTTCAACAA CGGATCTCTT GGTTCTGGCA | 240 |
| TCGATGAAGA ACGCAGCGAA ATGCGATAAG TAGTGTGAAT TGCAGAATTC AGTGAATCAT | 300 |
| CGAATCTTTG AACGCACATT GCGCCCTTTG GTATTCCAAA GGGCATGCCT GTTCGAGCGT | 360 |
| CATTTGTACC CTCAAGCTTT GCTTGGTGTT GGGCGTCTTG TCTCTCTCCC GAGACTCGCC | 420 |
| TTAAAATCAT TGGCAGCCGG CCTACTGGTT TCGGARCGCA GCACATTATT TGCGCTCTTG | 480 |
| TCCAGCCGCG GTCGCGCGTC CATGAAGCTT CTTTCAACCT TTTGACCTCG GATCAGGTAG | 540 |
| GGATACCCGC TGAACTTAAG CATATCAATA AGCGGAGGA | 579 |

(2) INFORMATION FOR SEQ ID NO:35:

(i) SEQUENCE CHARACTERISTICS:

```
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: 205

(vii) IMMEDIATE SOURCE:
        (B) CLONE: 4-2

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..208
        (D) OTHER INFORMATION: /note= "ITS1"

(ix) FEATURE:
        (A) NAME/KEY: misc_feature
        (B) LOCATION: 209..365
        (D) OTHER INFORMATION: /note= "5.8S rRNA gene"

(ix) FEATURE:
        (A) NAME/KEY: misc_feature
        (B) LOCATION: 366..527
        (D) OTHER INFORMATION: /note= "ITS2"

(ix) FEATURE:
        (A) NAME/KEY: misc_feature
        (B) LOCATION: 528..580
        (D) OTHER INFORMATION: /note= "5' end of large subunit
            rRNA gene"

(xi) SEQUENCE DESCRIPTION: SEQ ID NO:35:

TCCGTAGGTG AACCTGCGGA GGGATCATTA CACAAATATG AAGCCGGACT GGGATAGGGC    60

YTCGCTGCCT TGCCCGTCTG GCGCCATATT CACCCATGTC TTTTKGCGTA MTAMTTGTTT   120

CCTTGGCGGG TCCGCCCGCC AATTGGACCT TATTCAAACC TTTTTTTCAG TTGCAATCAG   180

CGTCAGCAAA ACAAATGTAA TCAATTACAA CTTTCAACAA CGGATCTCTT GGTTCTGGCA   240

TCGATGAAGA ACGCAGCGAA ATGCGATAAG TAGTGTGAAT TGCAGAATTC AGTGAATCAT   300

CGAATCTTTG AACGCACATT GCGCCCTTTG GTATTCCAAA GGGCATGCCT GTTCGAGCGT   360

CATTTGTACC CTCAAGCTTT GCTTGGTGTT GGGCGTCTTG TCTCTCTCCC GAGACTCGCC   420

TTAAAATCAT TGGGCAGCCG GCCTACTGGT TTCGGAGMGC AGCACATTAT TTGCGCTCTT   480

GTCCAGCCGC GGTCGCGCGT CCATGAAGCT TCTTTCAACC TTTTGACCTC GGATCAGGTA   540

GGGATACCCG CTGAACTTAA GCATATCAAT AAGCGGAGGA                         580

(2) INFORMATION FOR SEQ ID NO:36:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: 403

(vii) IMMEDIATE SOURCE:
```

(B) CLONE: 5-2

(ix) FEATURE:
                (A) NAME/KEY: misc_feature
                (B) LOCATION: 1..30
                (D) OTHER INFORMATION: /note= "3' end of small subunit
                    rRNA gene"

(ix) FEATURE:
                (A) NAME/KEY: misc_feature
                (B) LOCATION: 31..208
                (D) OTHER INFORMATION: /note= "ITS1"

(ix) FEATURE:
                (A) NAME/KEY: misc_feature
                (B) LOCATION: 209..365
                (D) OTHER INFORMATION: /note= "5.8S rRNA gene"

(ix) FEATURE:
                (A) NAME/KEY: misc_feature
                (B) LOCATION: 366..526
                (D) OTHER INFORMATION: /note= "ITS2"

(ix) FEATURE:
                (A) NAME/KEY: misc_feature
                (B) LOCATION: 527..579
                (D) OTHER INFORMATION: /note= "5' end of large subunit
                    rRNA gene"

(xi) SEQUENCE DESCRIPTION: SEQ ID NO:36:

TCCGTAGGTG AACCTGCGGA GGGATCATTA CACAAATATG AAGCCGGACT GGGATAGGGC      60

CTCGCTGCCT TGCCCGTCTG GCGCCATATT CACCCATGTC TTTTTGCGTA CTACTTGTTT     120

CCTTGGCGGG TCCGCCCGCC AATTGGACCT TATTCAAACC TTTTTTTCAG TTGCAATCAG     180

CGTCAGCAAA ACAAATGTAA TCAATTACAA CTTTCAACAA CGGATCTCTT GGTTCTGGCA     240

TCGATGAAGA ACGCAGCGAA ATGCGATAAG TAGTGTGAAT TGCAGAATTC AGTGAATCAT     300

CGAATCTTTG AACGCACATT GCGCCCTTTG GTATTCCAAA GGGCATGCCT GTTCGAGCGT     360

CATTTGTACC CTCAAGCTTT GCTTGGTGTT GGGCGTCTTG TCTCTCTCCC GAGACTCGCC     420

TTAAAATCAT TGGCAGCCGG CCTACTGGTT TCGGAGCGCA GCACATTATT TGCGCTCTTG     480

TCCAGCCGCG GTCGCGCGTC CATGAAGCTT CTTTCAACCT TTTGACCTCG GATCAGGTAG     540

GGATACCCGC TGAACTTAAG CATATCAATA AGCGGAGGA                            579

(2) INFORMATION FOR SEQ ID NO:37:

(i) SEQUENCE CHARACTERISTICS:
            (A) LENGTH: 580 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pyrenophora tritici-repentis
            (C) INDIVIDUAL ISOLATE: 109

(vii) IMMEDIATE SOURCE:
            (B) CLONE: 6-2

(ix) FEATURE:
            (A) NAME/KEY: misc_feature
            (B) LOCATION: 1..30
            (D) OTHER INFORMATION: /note= "3' end of small subunit
                rRNA gene"

(ix) FEATURE:
            (A) NAME/KEY: misc_feature
            (B) LOCATION: 31..209
            (D) OTHER INFORMATION: /note= "ITS1"

```
        (ix) FEATURE:
             (A) NAME/KEY: misc_feature
             (B) LOCATION: 210..366
             (D) OTHER INFORMATION: /note= "5.8S rRNA gene"

(ix) FEATURE:
             (A) NAME/KEY: misc_feature
             (B) LOCATION: 367..527
             (D) OTHER INFORMATION: /note= "ITS2"

(ix) FEATURE:
             (A) NAME/KEY: misc_feature
             (B) LOCATION: 528..580
             (D) OTHER INFORMATION: /note= "5' end of large subunit
                 rRNA gene"

(xi) SEQUENCE DESCRIPTION: SEQ ID NO:37:

TCCGTAGGTG AACCTGCGGA GGGATCATTA CACAAATATG AAGCCGGACT GGGATAGGGC    60

CTCGCTGCCT TGCCCGTCTG GCGCCATATT CACCCATGTC TTTTTGCGTA CTACTTGTTT   120

CCTTGGCGGG TCCGCCCGCC AATTGGACCT TATTCAAACC TTTTTTTNCA GTTGCAATCA   180

GSGTCAGCAA AACAAATGTA ATCAATTACA ACTTTCAACA ACGGATCTCT TGGTTCTGGC   240

ATCGATGAAG AACGCAGCGA AATGCGATAA GTAGTGTGAA TTGCAGAATT CAGTGAATCA   300

TCGAATCTTT GAACGCACAT TGCGCCCTTT GGTATTCCAA AGGGCATGCC TGTTCGAGCG   360

TCATTTGTAC CCTCAAGCTT TGCTTGGTGT TGGGTGTCTT GTCTCTCTCC CGAGACTCGC   420

CTTAAAATCA TTGGCAGCCG GCCTACTGGT TTCGGAGCGC AGCACATTAT TTGCGCTCTT   480

GTYCARCCGC GGTCGCGCGT CCATGAAGCT TCTTTCAACC TTTTGACCTC GGATCAGGTA   540

GGGATACCCG CTGAACTWAA GCATATCAAT AAGCGGARGA                         580

(2) INFORMATION FOR SEQ ID NO:38:

(i) SEQUENCE CHARACTERISTICS:
          (A) LENGTH: 579 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Pyrenophora tritici-repentis
          (C) INDIVIDUAL ISOLATE: 407

(vii) IMMEDIATE SOURCE:
          (B) CLONE: 7-3-2

(ix) FEATURE:
          (A) NAME/KEY: misc_feature
          (B) LOCATION: 1..30
          (D) OTHER INFORMATION: /note= "3' end of small subunit
              rRNA gene"

(ix) FEATURE:
          (A) NAME/KEY: misc_feature
          (B) LOCATION: 31..208
          (D) OTHER INFORMATION: /note= "ITS1"

(ix) FEATURE:
          (A) NAME/KEY: misc_feature
          (B) LOCATION: 209..365
          (D) OTHER INFORMATION: /note= "5.8S rRNA gene"

(ix) FEATURE:
          (A) NAME/KEY: misc_feature
          (B) LOCATION: 366..526
          (D) OTHER INFORMATION: /note= "ITS2"

(ix) FEATURE:
```

```
            (A) NAME/KEY: misc_feature
            (B) LOCATION: 527..579
            (D) OTHER INFORMATION: /note= "5' end of large subunit
                rRNA gene"

(xi) SEQUENCE DESCRIPTION: SEQ ID NO:38:

TCCGTAGGTG AACCTGCGGA GGGATCATTA CACAAATATG AAGCCGGACT GGGATAGGGC      60

CTCGCTGCCT TGCCCGTCTG GCGCCATATT CACCCATGTC TTTTTGCGTA CTACTTGTTT     120

CCTTGGCGGG TCCGCCCGCC AATTGGACCT TATTCAAACC TTTTTTTCAG TTGCAATCAG     180

CGTCAGCAAA ACAAATGTAA TCAATTACAA CTTTCAACAA CGGATCTCTT GGTTCTGGCA     240

TCGATGAAGA ACGCAGCGAA ATGCGATAAG TAGTGTGAAT TGCAGAATTC AGTGAATCAT     300

CGAATCTTTG AACGCACATT GCGCCCTTTG GTATTCCAAA GGGCATGCCT GTTCGAGCGT     360

CATTTGTACC CTCAAGCTTT GCTTGGTGTT GGGCGTCTTG TCTCTCTCCC GAGACTCGCC     420

TTAAAATCAT TGGCAGCCGG CCTACTGGTT TCGGAGCGCA GCACATTATT TGCGCTCTTG     480

TYCAGCCGCG GTCGCGCGTC CATGAAGCTT CTTTCAACCT TTTGACCTCG GATCAGGTAG     540

GGATACCCGC TGAACTTAAG CATATCAATA AGCSGARGA                            579

(2) INFORMATION FOR SEQ ID NO:39:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: 1316

(vii) IMMEDIATE SOURCE:
        (B) CLONE: 8-1

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..208
        (D) OTHER INFORMATION: /note= "ITS1"

(ix) FEATURE:
        (A) NAME/KEY: misc_feature
        (B) LOCATION: 209..367
        (D) OTHER INFORMATION: /note= "5.8S rRNA gene"

(ix) FEATURE:
        (A) NAME/KEY: misc_feature
        (B) LOCATION: 368..534
        (D) OTHER INFORMATION: /note= "ITS2"

(ix) FEATURE:
        (A) NAME/KEY: misc_feature
        (B) LOCATION: 535..587
        (D) OTHER INFORMATION: /note= "5' end of large subunit
            rRNA gene"

(xi) SEQUENCE DESCRIPTION: SEQ ID NO:39:

TCCGTAGGTG AACCTGCGGA NGGATCATWA CACAAATATG ARNCCGGACT GGGATAGGGC      60

CTCGCTGCCT TGCCCGTCTG GCGCCATATT CACCCATGTY TNTTTGCGTA CTAMTTGTTT     120

CCTTGGCGGG TCCGCCCGCC AATTGGACCT TATTCAAACC TTTTTTTCAG TTGCAATCAG     180
```

```
CGTCAGCAAA ACAAATGTAA TCAATTACAA CTTTCAACAA CGGATCTCTT GGTTCTGGCA      240

TCGATGAAGA ACSCAGCGAA ATGCGATAAG TAGTGTGAAT TGCAGAATTC AGTGCAATCA      300

TCGAATCTTT GAAACGCACA TTGCGCCCTT TGGTATWCCA AAGGGCATGC CTGTTCGAGC      360

GTCATTTGTA CCCTCCAAGC TTTGCCTTGG GTGTTGGGCG TCTTGTCTCT CTCCCSAGAC      420

TCGCYTTAAA ATCATTGGGC AGCSGGCCTA CTGGTTTCCG GAGCGCARCA MATTTATTTG      480

CSCTCTTGTC MASCCGCGGT CGCGCGTCCA TGAARCTTCT TYCAACCTTT TGACCTCGGA      540

TCAGGTAGGG ATACCCGCTG AACTTAAGCA TATCAATAAG CGGAGGA                   587
```

(2) INFORMATION FOR SEQ ID NO:40:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora tritici-repentis
        (C) INDIVIDUAL ISOLATE: 223

(vii) IMMEDIATE SOURCE:
        (B) CLONE: 9-2

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..208
        (D) OTHER INFORMATION: /note= "ITS1"

(ix) FEATURE:
        (A) NAME/KEY: misc_feature
        (B) LOCATION: 209..365
        (D) OTHER INFORMATION: /note= "5.8S rRNA gene"

(ix) FEATURE:
        (A) NAME/KEY: misc_feature
        (B) LOCATION: 366..527
        (D) OTHER INFORMATION: /note= "ITS2"

(ix) FEATURE:
        (A) NAME/KEY: misc_feature
        (B) LOCATION: 528..580
        (D) OTHER INFORMATION: /note= "5' end of large subunit
            rRNA gene"

(xi) SEQUENCE DESCRIPTION: SEQ ID NO:40:

```
TCCGTAGGTG AACCTGCGGA GGGATCATTA CACAAATATG AAGCCGGACT GGGATAGGGC       60

CTCGCTGCCT TGCCCGTCTG GCGCCATATT CACCCATGTC TTTTTGSGTA CTACTKGTTT      120

CCTTGGCGGG TCCGCCCGCC AATTGGACCT TATTCAAACY TTTTTTTCAG TTGCAATCAG      180

CGTCAGCAAA ACAAATGTAA TCAATKACAA CTTTCAACAA CGGATCTCTC GGTTCTGGCA      240

TCGATGAAGA ACGCAGCGAA ATGCGATAAG TAGTGTGAAT TGCAGAATTC AGTGAATCAT      300

CGAATCTTTG AACGCACATT GCGCCCTTTG GTATTCCAAA GGGCATGCCT GTTCGAGCGT      360

CATTTGTACC CTCAAGCTTT GCTTGGTGTT GGGCGTCTTG TCTCTCTCCC GARACTCGCC      420

TTAAAATCAT TGGCAGCCGG CCTACTGGTT TCGGAGCGCA GCACATTATT TGCGCTCTTG      480

TCCAGCCGCG GTCCSCSCGT CCATGAAGCT TCTTTCAACC TTTTGAMCTC GGATCAGGTA      540
```

```
GGGATACCCG CTGAACTTAA GCATATCAAT AAGCGGAGGA                         580
```

(2) INFORMATION FOR SEQ ID NO:41:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pyrenophora teres
        (C) INDIVIDUAL ISOLATE: 36570

(vii) IMMEDIATE SOURCE:
        (B) CLONE: 10-1

(ix) FEATURE:
        (A) NAME/KEY: misc_feature
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..209
        (D) OTHER INFORMATION: /note= "ITS1"

(ix) FEATURE:
        (A) NAME/KEY: misc_feature
        (B) LOCATION: 210..366
        (D) OTHER INFORMATION: /note= "5.8S rRNA gene"

(ix) FEATURE:
        (A) NAME/KEY: misc_feature
        (B) LOCATION: 367..536
        (D) OTHER INFORMATION: /note= "ITS2"

(ix) FEATURE:
        (A) NAME/KEY: misc_feature
        (B) LOCATION: 537..590
        (D) OTHER INFORMATION: /note= "5' end of large subunit
            rRNA gene"

(xi) SEQUENCE DESCRIPTION: SEQ ID NO:41:

```
TCCGTAGGTG AACCTGCGGA GGGATCATTA CACAAATATG AAGGCAGATT GGGTAGTCCC    60

CGSTTTTGGG GGTTTGCCCA TTCTGGCGCC ATATTCACCC ATGTCTTTTG CGTACTACTT   120

GTTTCCTTGG CGGGCTCGCC CGCCAATTGG ACTTTATTCA AACCTTTTTT TATTGCAATC   180

AGCGTCAGCA AAACAATGTA ATCAATTACA ACTTTCAACA ACGGATCTCT TGGTTCTGGC   240

ATCGATGAAG AACGCAGCGA AATGCGATAA GTAGTGTGAA TTGCAGAATT CAGTGAATCA   300

TCGAATCTTT GAACGCACAT TGCGCCCTTT GGTATTCCAA AGGGCATGCC TGTTCGAGCG   360

TCATTTGTAC CCTCAAGCTT TGCTTGGTGT TGGGCGTCTT TTGTCTCTCC CCCGAGACTC   420

GCCTTAAAAA CATTGGCAGC CGGCCTACTG GTTTCGGAGC GCAGCACATT ATTTGCGCTC   480

TTGTYCAGCC GCGGTCGCGC GTCCATGAAG CCTTTTTTTT TTTTCAGCCT TTTGACTCTC   540

GGATCAGGTA GGGATACCCG CTGAACTTAA GCATATCAAT AAGCGGAGGA              590
```